US011642387B2

(12) United States Patent
Cho et al.

(10) Patent No.: US 11,642,387 B2
(45) Date of Patent: May 9, 2023

(54) COMPOSITION FOR PREVENTING OR INHIBITING INFLUENZA VIRUS INFECTION, CONTAINING GINSENG BERRY POLYSACCHARIDES

(71) Applicant: AMOREPACIFIC CORPORATION, Seoul (KR)

(72) Inventors: Donghyun Cho, Yongin-si (KR); Suhwan Kim, Yongin-si (KR); Juewon Kim, Yongin-si (KR); Chan Woong Park, Yongin-si (KR); Dae Bang Seo, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 106 days.

(21) Appl. No.: 17/051,990

(22) PCT Filed: Apr. 26, 2019

(86) PCT No.: PCT/KR2019/005081
§ 371 (c)(1),
(2) Date: Oct. 30, 2020

(87) PCT Pub. No.: WO2019/212203
PCT Pub. Date: Nov. 7, 2019

(65) Prior Publication Data
US 2021/0196776 A1   Jul. 1, 2021

(30) Foreign Application Priority Data

May 2, 2018   (KR) .................. 10-2018-0050593
Apr. 25, 2019  (KR) .................. 10-2019-0048626

(51) Int. Cl.
A61K 36/258   (2006.01)
A23L 33/105   (2016.01)
A61P 31/16    (2006.01)
A61K 9/00     (2006.01)
A61K 31/715   (2006.01)

(52) U.S. Cl.
CPC .......... *A61K 36/258* (2013.01); *A23L 33/105* (2016.08); *A61K 9/0053* (2013.01); *A61K 31/715* (2013.01); *A61P 31/16* (2018.01); *A61K 2236/331* (2013.01)

(58) Field of Classification Search
None
See application file for complete search history.

(56) References Cited

U.S. PATENT DOCUMENTS

2017/0189464 A1    7/2017  Lee et al.
2021/0128660 A1*   5/2021  Kim .................. A23L 2/52

FOREIGN PATENT DOCUMENTS

| CN | 1821275       | * | 8/2006  |
| CN | 103705561     | * | 4/2014  |
| CN | 103705561     | A |   4/2014  |
| CN | 2016106317253 | * | 1/2017  |
| EP | 3581192       | A1|  12/2019 |
| JP | 2011/513294   | * | 4/2001  |
| JP | 2005-531576   | A |  10/2005 |
| JP | 2007/507441   | * | 3/2007  |
| JP | 2007-507441   | A |   3/2007 |
| JP | 2011-513294   | A |   4/2011 |
| JP | 2016-515549   | A |   5/2016 |
| KR | 10-2003-0091665 | A1 | 12/2003 |
| KR | 10-0797016    | B1|   1/2008 |
| KR | 10-2009-0037595 | A |  4/2009 |
| KR | 10-2010-0124304 | A | 11/2010 |
| KR | 10-2014-0143115 | A | 12/2014 |
| KR | 10-2018-0088214 | A |  8/2018 |
| WO | 02/38166      | A2|   5/2002 |
| WO | 03/099308     | A1|  12/2003 |
| WO | 2005/039320   | A2|   5/2005 |
| WO | 2009/106975   | A2|   9/2009 |
| WO | 2013/135395   | A1|   9/2013 |
| WO | 2016/003063   | A1|   1/2016 |

OTHER PUBLICATIONS

Yoo, D. et. al. Protective Effect of Ginseng Polysaccharides on Influenza Viral Infection. PLoS ONE, 7(3)1-7, Mar. 2012. (Year: 2012).*
Mousa, H. Prevention and Treatment of Influenza . . . J of Evidence Based Complementary & Alternative Medicine 22(1)166-174, 2017. (Year: 2017).*
Kim, J. et al. Ginseng Berry and its Biological Effects as a Natural Phytochemical. Natural Products Chemistry & Research 4(2)1-4, 2016. (Year: 2016).*
Gerrit-Jan Van Holst et al., "Quantification of Arabinogalactan-Protein in Plant Extracts by Sinble Radial Gel Diffusion", Analytical Biochemistry, 148:446-450 (1985).
Yunjeong Kim et al., "Inhibition of Influenza virus replication by plant-derived isoquercetin", Elsevier, Antiviral Research 88: 227-235 (2010).
Dae-Goon Yoo et al., "Protective Effect of Ginseng Polysaccharides on Influenza Viral Infection", Plos One, vol. 7, No. 3: e33678 (2012).
Yingyu Wang et al., "Extraction, characterization of a Ginseng fruits polysaccharide and its immune modulating activities in rats with Lewis lung carcinoma", Carbohydrate Polymers, vol. 127: 215-221 (2015).
Miseon Kim et al., "Effect of polysaccharides from a Korean ginseng berry on the immunosenescence of aged mice", Journal of Ginseng Research, vol. 42: 447-454 (2017).
International Search Report and Written Opinion for PCT/KR2019/005081, dated Aug. 1, 2019.

(Continued)

*Primary Examiner* — Ralph J Gitomer

(74) *Attorney, Agent, or Firm* — Merchant & Gould P.C.

(57)  ABSTRACT

Disclosed is a composition for preventing or inhibiting influenza virus infection, containing *ginseng* berry polysaccharides as active ingredients, and the *ginseng* berry polysaccharides exhibit an inhibitory effect on influenza virus activity or infection due to specific ingredients and structures and, specifically, have an excellent inhibitory effect on neuraminidase activity.

8 Claims, 21 Drawing Sheets

(56) References Cited

OTHER PUBLICATIONS

Office Action for Japanese Patent Application No. 2020-560975 (dated Sep. 27, 2022).
Wei Yang et al., "Study on Influenza Virus Neuraminidase Detection and Inhibitory Action by Ginseng polysaccharide", Proceeding of Outstanding Doctoral Dissertation (Ph.D.) Agricultural Science and Technology in China, vol. 5, pp. 83 and pp. 92-94 (2013) (See Brief Translation from Chinese Office Action).
Doudechiang et al., "Study on Chinese Pillar ginseng (ShiZhu Ginseng) and related Chinese medicine", Liaoning Science and Technology Publishing house, pp. 473, ISBN 978-7-5381-9790-7 (2016) (See Brief Translation from Office Action).
Office Action for Chinese Application No. 201980044814.6 (dated Nov. 22, 2021).
Search report for European Patent Application No. 19796078.4 (dated Jan. 31, 2022).

* cited by examiner

CVT

APGP

FIG. 18

COMPOSITION FOR PREVENTING OR INHIBITING INFLUENZA VIRUS INFECTION, CONTAINING GINSENG BERRY POLYSACCHARIDES

CROSS-REFERENCE TO RELATED APPLICATIONS

This application is a National Stage Application of PCT/KR2019/005081, filed Apr. 26, 2019, which claims benefit of priority to Serial No. 10-2018-0050593, filed May 2, 2018 and Serial No. 10-2019-0048626, filed Aril 25, 2019 in the Republic of Korea and which applications are incorporated herein by reference. To the extent appropriate, a claim of priority is made to each of the above disclosed applications.

TECHNICAL FIELD

The present disclosure discloses a composition for preventing or inhibiting influenza virus infection, which contains *ginseng* berry polysaccharides.

BACKGROUND ART

Influenza is called a bad cold because the early symptoms of infection are similar to those of common cold (acute viral nasopharyngitis). However, it is a totally different disease in causes and symptoms. Unlike cold which is mainly caused by rhinoviruses, coronaviruses, adenoviruses, respiratory syncytial virus, etc., influenza is caused by influenza virus.

Influenza causes severe symptoms such as fever, chills, muscle pain and joint pain, and may lead to death due to the high risk of high fever and complications. Since influenza pandemics by highly pathogenic or highly infectious novel or mutant influenza viruses can result in huge deaths, countermeasures are required.

Influenza can be treated by directly blocking the activity or infection mechanism of the virus by targeting the influenza virus itself. As therapeutic agents for influenza, M2 inhibitors such as amantadine and rimantadine and neuraminidase (NA) inhibitors such as Relenza® (zanamivir) and Tamiflu® (oseltamivir) are commercially available. The M2 inhibitors act only on influenza A viruses, while the NA inhibitors are effective both for influenza A and B viruses. Tamiflu has side effects such as nausea, vomiting, neurological or psychiatric disfunctions, etc., and resistance patterns have been reported about the commercially available therapeutic agents including Tamiflu.

Therefore, a substance with no side effect or resistance, which has a superior therapeutic effect of preventing or treating by inhibiting influenza virus infection, is necessary.

DISCLOSURE

Technical Problem

In an aspect, the present disclosure is directed to providing a composition for preventing or inhibiting influenza infection effectively without side effect.

In another aspect, the present disclosure is directed to providing a composition acting as an influenza-targeting therapeutic agent.

In another aspect, the present disclosure is directed to providing a composition capable of preventing or inhibiting influenza virus infection by blocking the infection mechanism of influenza virus.

In another aspect, the present disclosure is directed to providing a composition exhibiting an effect of inhibiting influenza virus infection by inhibiting neuraminidase activity.

In another aspect, the present disclosure is directed to providing a composition for preventing or inhibiting influenza virus infection that can act on both influenza A and B viruses.

In another aspect, the present disclosure is directed to providing a composition exhibiting a remarkably superior effect of preventing or inhibiting influenza virus infection at a low administration dose.

In another aspect, the present disclosure is directed to providing a composition for preventing or inhibiting influenza infection, which has no or few side effects as a natural product and is free from resistance.

Technical Solution

In an exemplary embodiment, the present disclosure a composition for preventing or inhibiting influenza virus infection, which contains *ginseng* berry polysaccharides.

Advantageous Effects

In an aspect, the present disclosure provides a composition for preventing or inhibiting influenza infection effectively with no side effect.

In another aspect, the present disclosure provides a composition which acts as an influenza-targeting therapeutic agent.

In another aspect, the present disclosure provides a composition capable of preventing or inhibiting influenza virus infection by blocking the infection mechanism of influenza virus.

In another aspect, the present disclosure provides a composition which exhibits an effect of inhibiting influenza virus infection by inhibiting neuraminidase activity.

In another aspect, the present disclosure provides a composition for preventing or inhibiting influenza virus infection, which can act on both influenza A and B viruses.

In another aspect, the present disclosure provides a composition exhibiting a remarkably superior effect of preventing or inhibiting influenza virus infection at a low administration dose.

In another aspect, the present disclosure provides a composition for preventing or inhibiting influenza infection, which has no or few side effects as a natural product and is free from resistance.

BRIEF DESCRIPTION OF DRAWINGS

Figure 7:
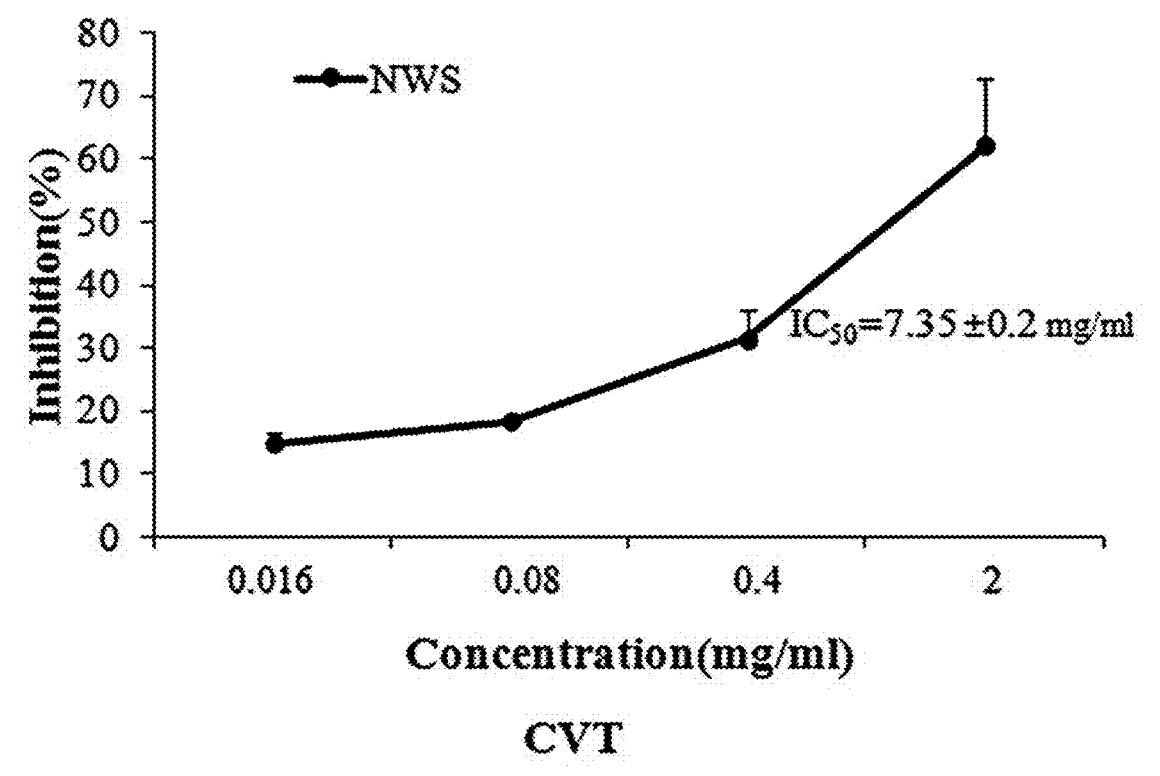

FIG. 7 shows a result of investigating inhibitory effect on neuraminidase activity upon inoculation of NWS virus to a CVT-treated group.

Figure 18:
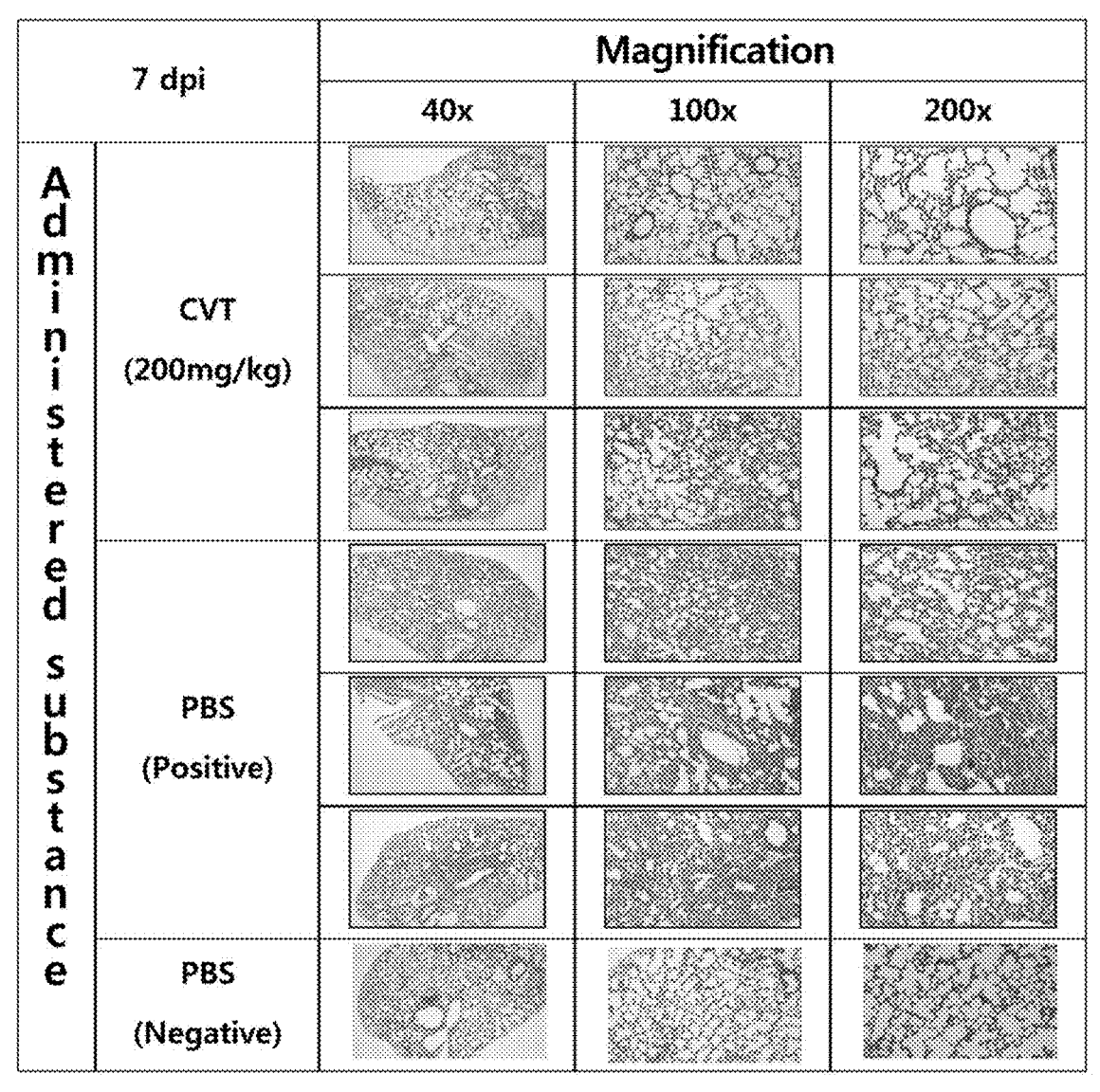

FIG. 18 shows the images of lung lesion tissue 7 days after inoculation of virus for a CVT-administered group, a positive control group and a negative control group.

BEST MODE

Figure 1:
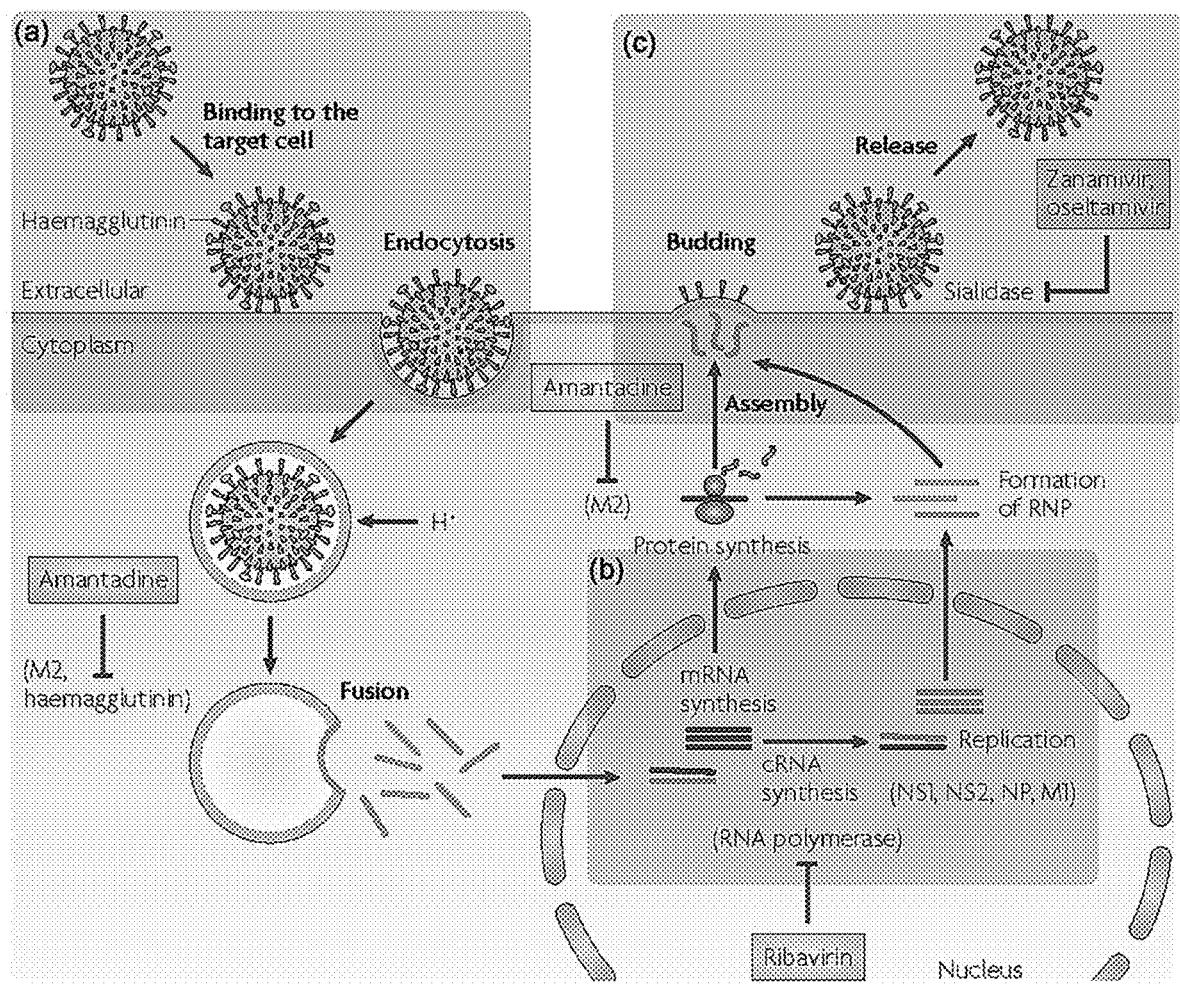
FIG. 1 schematically shows the influenza inhibition mechanisms of conventional influenza therapeutic agents showing (A) inhibition of hemagglutinin, (B) inhibition of mRNA synthesis, and (C) inhibition of neuraminidase.

Hereinafter, the exemplary embodiments of the present disclosure are described in detail referring to the attached drawings. However, the present disclosure is not limited to the exemplary embodiments described herein but may be embodied into various other forms. Rather, the exemplary embodiments are provided so that the present disclosure will be thorough and complete, and the inventive concept of the present disclosure will be fully conveyed to those skilled in the art. In the drawings, the size of each component, such as width, thickness, etc., is exaggerated to clearly express the component. In addition, although only a part of a component is shown in some cases for convenience of description, those skilled in the art will easily understand the rest of the component. In addition, one of ordinary skill in the art may implement the concept of the present disclosure in various other forms without departing from the technical concept of the present disclosure.

According to an exemplary embodiment of the present disclosure, a composition for preventing or inhibiting influenza virus infection, which contains *ginseng* berry polysaccharides as active ingredients, may be provided. The *ginseng* berry polysaccharides exhibit an inhibitory effect on influenza virus activity or infection due to specific ingredients and structures and, specifically, have an excellent inhibitory effect on neuraminidase activity. Therefore, the composition according to exemplary embodiments of the present disclosure can exhibit a superior effect of preventing or inhibiting influenza virus infection.

Influenza viruses are classified into types A, B, C, etc. Type A and type B are common, and influenza A virus is the most prevailing type. Influenza A virus is a single-stranded negative-sense RNA virus having an envelope, which belongs to the family Orthomyxoviridae. Its subtypes are determined by 16 kinds of hemagglutinin (H1 to H16) and 9 kinds of neuraminidase (N1 to N9), which are surface antigens.

FIG. 1 shows the influenza virus life cycle inhibition mechanisms of amantadine, Relenza® (zanamivir), Tamiflu® (oseltamivir) and ribavirin, which are conventional influenza therapeutic agents. The representative inhibition mechanisms of the conventional influenza virus-targeting therapeutic agents include (A) inhibition of hemagglutinin involved in the penetration of the virus into cells, (B) inhibition of mRNA synthesis, and (C) inhibition of neuraminidase involved in the release of the virus.

The *ginseng* berry polysaccharides according to an exemplary embodiment of the present disclosure can prevent the infection of other cells because it inhibits neuraminidase activity and thereby prevents the influenza virus from being released from the infected cells.

The *ginseng* berry polysaccharides according to an exemplary embodiment of the present disclosure exhibits antiviral effect by inhibiting the proliferation of influenza virus and, therefore, can exhibit an effect of preventing, inhibiting or treating influenza virus infection.

The influenza virus may be an influenza virus in which the infection is prevented or inhibited by the neuraminidase activity-inhibiting action of the *ginseng* berry polysaccharides and may be, for example, one or more of influenza A virus, influenza B virus or influenza C virus. The influenza virus may be influenza A virus. For example, it may be one or more influenza virus of H1N1, H1N2, H2N2, H3N2, H5N1, H6N1, H7N2, H7N3, H7N7, H7N9, H9N2 or H10N7.

The *ginseng* berry polysaccharides may be polysaccharide ingredients derived from the berry of the aerial part of *ginseng* (*Panax ginseng* C. A. Meyer). In an exemplary embodiment, the *ginseng* berry may encompass the pulp, rind or a portion including both the pulp and rind of *ginseng* berry.

After extracting *ginseng* berry using ethanol, the *ginseng* berry polysaccharides may be obtained from extracted insoluble ingredients not dissolved in ethanol. For example, only water-soluble ingredients may be separated from the ethanol-extracted insoluble ingredients by conducting extraction using water, and the *ginseng* berry polysaccharides contained in the water-soluble ingredients may be used as active ingredients. For example, the *ginseng* berry polysaccharides may be obtained by concentrating the water-soluble ingredients, precipitating the same with ethanol and then removing low-molecular-weight ingredients.

For example, after extracting *ginseng* berry with seeds removed using 50-100% ethanol, a water-soluble extract is obtained by extracting the extracted insoluble ingredients under heating with 3-10 volume equivalents of water. After concentrating the water-soluble extract to a solid content of 10-50 wt % and precipitating the same using 2-5 volume equivalents of ethanol, *ginseng* berry polysaccharides may be obtained by removing low-molecular-weight ingredients by separating with a molecular weight cut-off of 10,000-30,000. The removal of the low-molecular-weight ingredients may be carried out by filtration such as ultrafiltration using an ultrafiltration membrane, dialysis, 1-10 times repeated dissolution treatment with 2-10 volume equivalents of 50-100% ethanol, etc. In an exemplary embodiment, drying may be carried out after removing the low-molecular-weight ingredients. The drying may be performed by freeze-drying, hot-air drying, spray drying, vacuum drying, etc.

In an exemplary embodiment, an enzyme treatment may be further included before the water-soluble ingredients of the *ginseng* berry are extracted with water. The enzyme may be any enzyme used in food without limitation. For example, the enzyme may be selected from amylase, protease, pectinase, lipase, cellulase, xylanase, β-glucanase, or pullulanase. For example, the enzyme treatment may be performed at 40-60° C. for 10-60 minutes.

The *ginseng* berry polysaccharides may include arabinose, galactose, galacturonic acid and glucuronic acid.

In an exemplary embodiment, the galacturonic acid and the glucuronic acid may be contained at a combined content of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, 7 wt % or more, 8 wt % or more, 9 wt % or more, or 10 wt % or more, and 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, or 4 wt % or less, based on the total weight of the polysaccharides. For example, the content may be 0.1-25 wt % or 0.5-20 wt %.

The galacturonic acid may be contained in an amount of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, 7 wt % or more, 8 wt % or more, 9 wt % or more, or 10 wt % or more, and 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, or 4 wt % or less, based on the total weight of the polysaccharides. The content may be, for example, 0.1-20 wt %, 0.1-15 wt %, 1-5 wt %, 5-15 wt % or 0.5-5 wt %.

The glucuronic acid may be contained in an amount of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, or 7 wt % or more, and 10 wt % or less, 9 wt % or less, 8 wt % or less, 7 wt % or less, 6 wt % or less, 5 wt % or less, or 4 wt % or less, based on the total weight of the polysaccharides. The content may be, for example, 0.1-10 wt %, 0.5-5 wt % or 0.1-5 wt %.

In an exemplary embodiment, the arabinose may be contained in an amount of 2-30 wt % based on the total weight of the polysaccharides.

In an exemplary embodiment, the galactose may be contained in an amount of 5-50 wt % based on the total weight of the polysaccharides.

Figure 2:
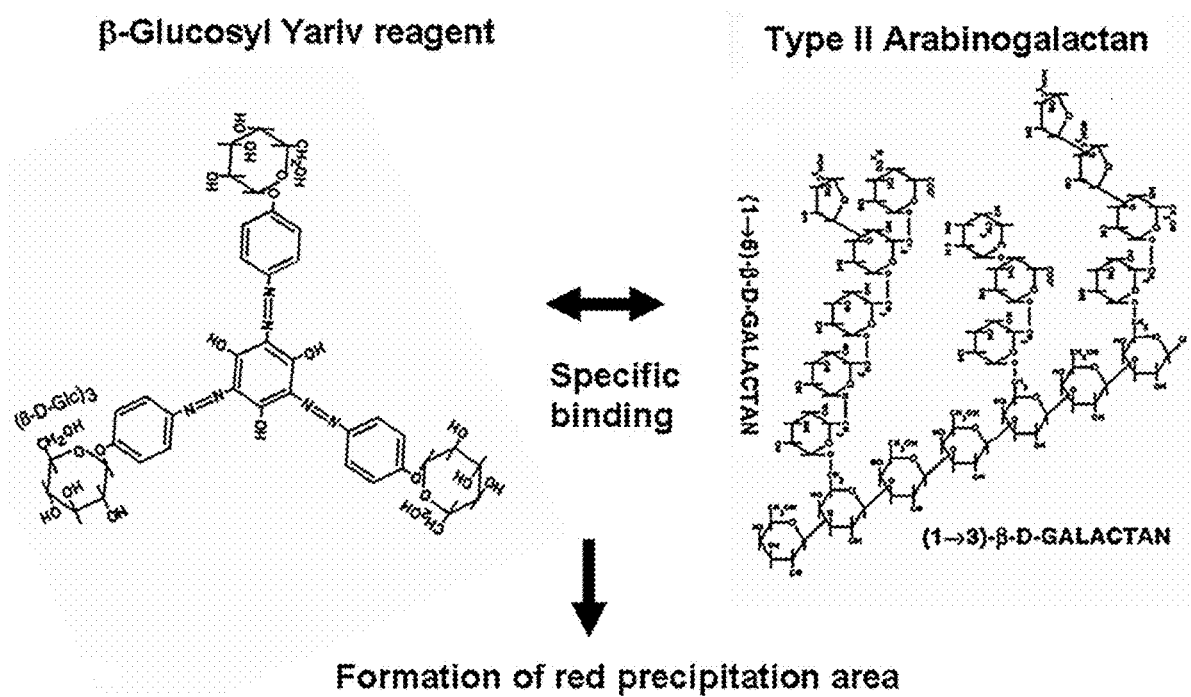
FIG. 2 schematically shows a reaction of detecting arabinogalactan using a β-glucosyl Yariv reagent.

The *ginseng* berry polysaccharides may contain an arabinogalactan structure at a high ratio. The arabinogalactan structure may be detected using a β-glucosyl Yariv reagent. FIG. 2 schematically shows a reaction of detecting arabinogalactan using a β-glucosyl Yariv reagent. The β-glucosyl Yariv reagent is 1,3,5-tri-(4-β-glucopyranosyl-oxyphenylazo)-2,4,6-trihydroxybenzene and forms a red precipitate by specifically reacting with type II arabino-β-3,6-galactan from among arabinogalactans. The area of a red precipitant ring produced by treatment with the β-glucosyl Yariv reagent is proportional to the concentration of the arabinogalactan structure in a concentration-dependent manner. The *ginseng* berry polysaccharides may exhibit a precipitant ring area of 40% or larger, 50% or larger, 60% or larger, 70% or larger or 80% or larger, and 90% or smaller, 80% or smaller, 70% or smaller or 60% or smaller with respect to the size of a precipitant ring produced by a reference arabino-β-3,6-galactan of the same concentration as 100%. For example, the precipitant ring area may be 50-90% or 50-80%.

The *ginseng* berry polysaccharides may have a weight-average molecular weight of 10 kDa or larger. The *ginseng* berry polysaccharides may have a main peak in a molecular weight range of 70-80 kDa.

The *ginseng* berry polysaccharides are a combination of various polysaccharide ingredients and exhibit a remarkable inhibitory effect on influenza virus activity or infection due to the synergistic effect of the ingredients contained therein. Specifically, they exhibit a superior effect of inhibiting neuraminidase activity.

The composition according to exemplary embodiments of the present disclosure may be provided as food additives or functional foods of various types containing the active ingredients. The composition may be processed into fermented milk, cheese, yogurt, juice, probiotics, health food, etc. containing the active ingredients and may also be used as various other food additives.

The composition according to exemplary embodiments of the present disclosure may be a health food composition.

The health food composition according to an exemplary embodiment of the present disclosure may contain the active ingredients in an amount of 0.0001-99 wt %, for example, 0.01-60 wt %, based on the total weight of the composition, although not being limited thereto.

The health food composition according to an exemplary embodiment of the present disclosure may be provided such that 0.001-500 mg, e.g., 0.005-100 mg, 0.01-50 mg or 0.01-10 mg, of the active ingredients are administered per day per kg body weight, once to several times a day. The composition may exhibit a significant effect even when the active ingredients are used in small amounts as described above.

In a specific exemplary embodiment, the health food composition may be formulated as a pill, a capsule, a tablet, a granule, a caramel, a drink, etc. In another exemplary embodiment, it may be processed into a liquid, a powder, a granule, a tablet, a tea bag, etc.

The composition may be administered via various methods such as simple drinking, injection, spraying, squeezing, etc.

The composition may contain other ingredients that can provide a synergistic effect to the main effect within a range not negatively affecting the main effect of the present disclosure. For example, it may further contain additives for improving physical properties such as a flavor, a colorant, a sterilizer, an antioxidant, an antiseptic, a wetting agent, a thickener, a mineral, an emulsifier, a synthetic polymer, etc. In addition, it may further contain auxiliary ingredients such as a water-soluble vitamin, an oil-soluble vitamin, a polypeptide, a polysaccharide, a seaweed extract, etc. These ingredients may be selected and mixed adequately by those skilled in the art depending on the formulation or purpose of use, and their addition amount may be selected within a range not negatively affecting the purpose and effect of the present disclosure. For example, the addition amount of these ingredients may be 0.01-5 wt %, e.g., 0.01-3 wt %, based on the total weight of the composition, although not being limited thereto.

In an exemplary embodiment of the present disclosure, the composition may be a pharmaceutical composition.

In an exemplary embodiment, the composition may be a composition for preventing or reducing influenza virus infection or for treating influenza, which contains *ginseng* berry polysaccharides.

In an exemplary embodiment, the composition may be a composition for preventing or treating a disease caused by influenza virus infection. The disease caused by influenza virus infection may include bad cold, sore throat, bronchitis, pneumonia, etc., although not being limited thereto.

The pharmaceutical composition may be various formulations for oral or parenteral administration. The formulations are prepared using a commonly used diluent or excipient such as a filler, an extender, a binder, a wetting agent, a disintegrant, a surfactant, etc. Solid formulations for oral administration include a tablet, a pill, a powder, a granule, a soft or hard capsule, etc. These solid formulations are prepared by mixing one or more compound with at least one or more excipient, e.g., starch, calcium carbonate, sucrose, lactose, gelatin, etc. In addition to simple excipients, a lubricant such as magnesium stearate, talc, etc. is also used. Liquid formulations for oral administration include a suspension, a solution for internal use, an emulsion, a syrup, etc. In addition to a commonly used simple diluent such as water and liquid paraffin, various excipients such as a wetting agent, a sweetener, an aromatic, a preservative, etc. may be contained. Formulations for parenteral administration include a sterilized aqueous solution, a non-aqueous solvent, a suspension, an emulsion, a freeze-dried formulation and a suppository. As the non-aqueous solvent or a solvent for the suspension, propylene glycol, polyethylene glycol, a vegetable oil such as olive oil, an injectable ester such as ethyl oleate, etc. may be used. As a base of the suppository, witepsol, macrogol, Tween 61, cocoa butter, laurin butter, glycerogelatin, etc. may be used.

The composition according to exemplary embodiments of the present disclosure may also contain the active ingredients in the form of pharmaceutically acceptable salts and may contain them either alone or in combination with other pharmaceutically active compounds. The salt is not specially limited as long as it is pharmaceutically acceptable. For example, hydrochloride, sulfate, nitrate, phosphate, hydrofluoride, hydrobromide, formate acetate, tartrate, lactate, citrate, fumarate, maleate, succinate, methanesulfonate, benzenesulfonate, toluenesulfonate, naphthalenesulfonate, etc. may be used.

The composition according to exemplary embodiments of the present disclosure may be administered parenterally or orally depending on purposes. A dosage of 0.001-500 mg, e.g., 0.005-100 mg, 0.01-50 mg or 0.01-10 mg, per kg body weight per day may be administered once or several times a day. The administration dosage for a particular patient can vary depending on the body weight, age, sex, health condition and diet of the patient, administration time, administration method, rate of excretion, severity of a disease, etc.

The pharmaceutical composition according to exemplary embodiments of the present disclosure may be formulated into an oral formulation such as a powder, a granule, a tablet, a soft or hard capsule, a suspension, an emulsion, a syrup, an aerosol, etc. or any form suitable for pharmaceutical preparations such as a formulation for external application to skin, e.g., an ointment, a cream, etc., a suppository, an injectable formulation, a sterilized solution for injection, etc. according to common methods.

According to another exemplary embodiment of the present disclosure, there may be provided a use of the *ginseng* berry polysaccharides for preventing or inhibiting influenza virus infection. The use may include a use for reducing influenza infection, a use for treating influenza or a use for preventing or treating a disease caused by influenza virus infection. Description about the *ginseng* berry polysaccharides, the effect, mode of administration, etc. of the *ginseng* berry polysaccharides will be omitted because it is the same as given above.

According to another exemplary embodiment of the present disclosure, there may be provided a use of *ginseng* berry polysaccharides for preparing a composition for preventing or inhibiting influenza virus infection, which contains the *ginseng* berry polysaccharides. The use may include a use for reducing influenza infection, a use for treating influenza or a use for preventing or treating a disease caused by influenza virus infection. Description about the *ginseng* berry polysaccharides, the effect, mode of administration, etc. of the *ginseng* berry polysaccharides will be omitted because it is the same as given above.

According to another exemplary embodiment of the present disclosure, there may be provided a method for preventing influenza virus infection, a method for inhibiting influenza virus, a method for reducing influenza infection or a method for treating influenza, which includes administering the *ginseng* berry polysaccharides to a subject. The method may include a method for preventing or treating a disease caused by influenza virus infection. The method may include administering a composition as described above containing the *ginseng* berry polysaccharides to a subject. Description about the *ginseng* berry polysaccharides, the effect, mode of administration, etc. of the *ginseng* berry polysaccharides will be omitted because it is the same as given above.

In an exemplary embodiment, the method may include administering the *ginseng* berry polysaccharides to a subject in need of inhibition of influenza virus, reduction of influenza infection or treatment of influenza. The administration may include administering an effective amount of the *ginseng* berry polysaccharides to the subject.

MODE FOR INVENTION

Hereinafter, the present disclosure will be described in detail through examples. However, the following examples are for illustrative purposes only and it will be obvious to one of ordinary skill in the art that the scope of the present disclosure is not limited by the examples.

[Preparation Example 1] Preparation of Ginseng Berry Polysaccharides

Figure 3:
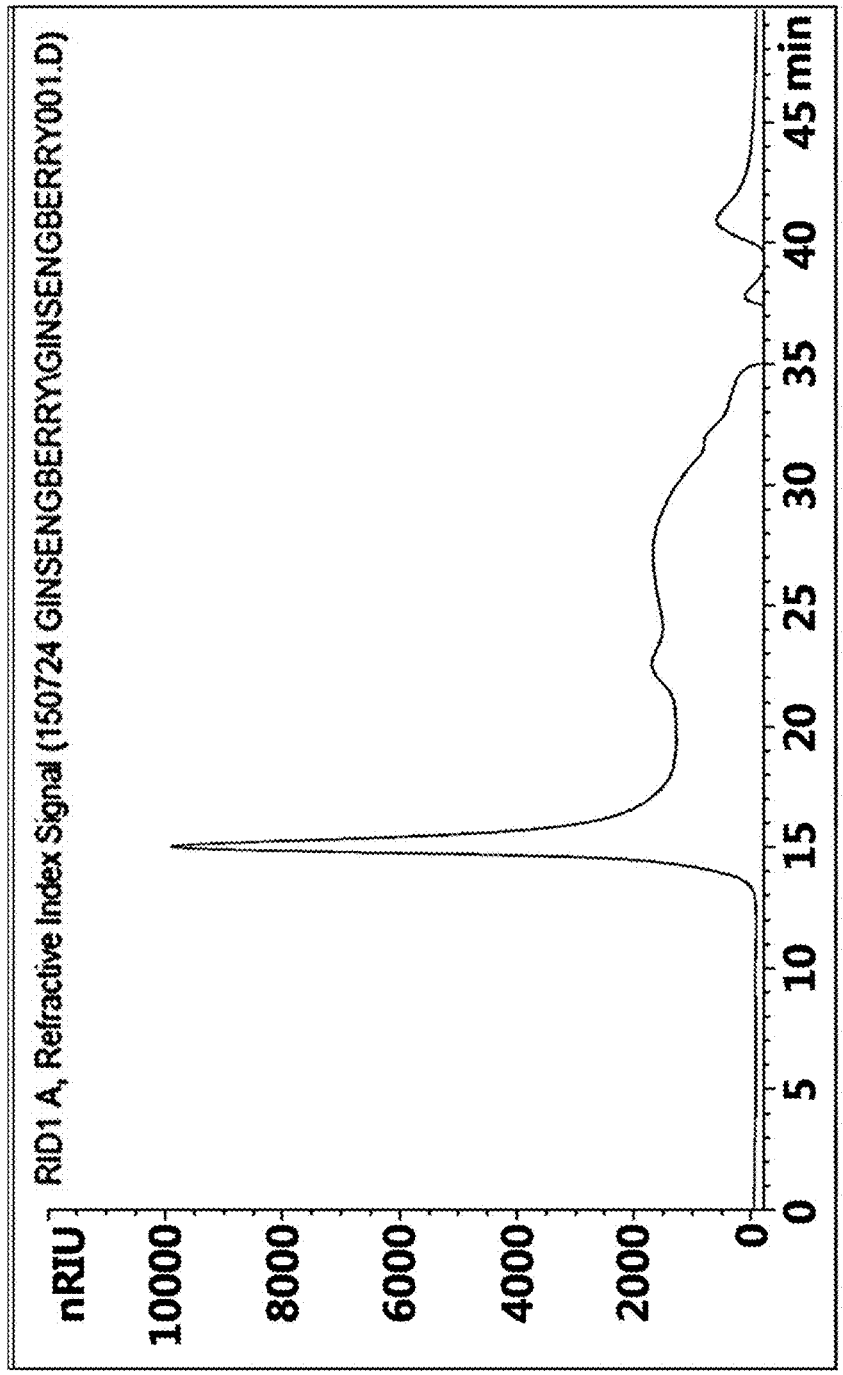
FIG. 3 shows the water-soluble fractions of *ginseng* berry.
Figure 4:
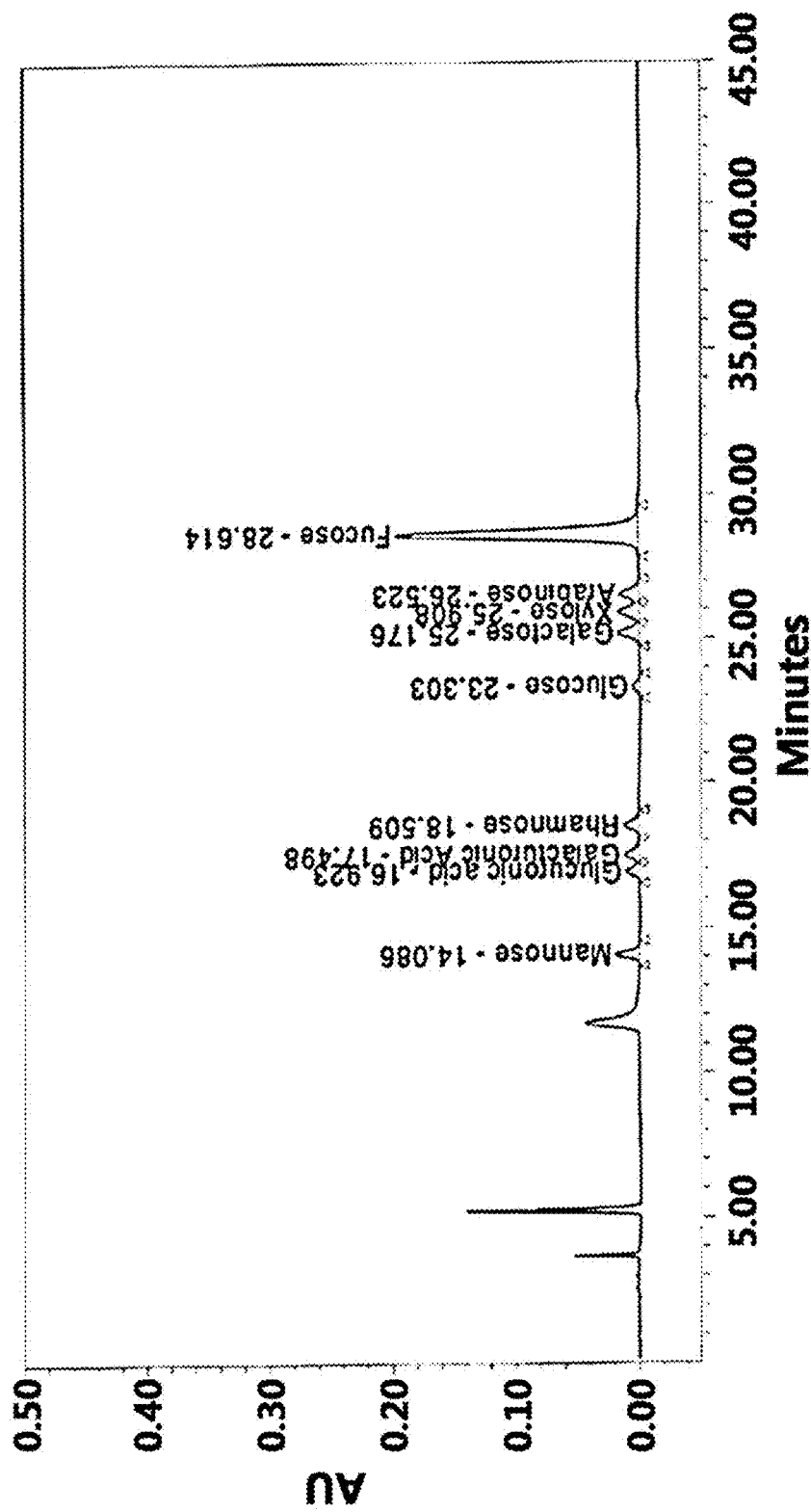
FIG. 4 shows a chromatography result of *ginseng* berry polysaccharides.

Ginseng berry with seeds removed was extracted using 10 volume equivalents of 90% ethanol to precipitate water-soluble ingredients and the supernatant was removed. The precipitated insoluble ingredients were extracted with 20 volume equivalents of water while heating at 90° C. for 5 hours. The obtained extract was concentrated to a solid content of 30 wt % and then precipitated by adding 2 volume equivalents of 90% ethanol. A high-performance liquid chromatography (HPLC) result of the precipitated water-soluble ingredients is shown in FIG. 3. After separating the precipitate through ultrafiltration to a molecular weight cut-off of 20,000 to remove low-molecular-weight ingredients, *ginseng* berry polysaccharides with a molecular weight of 10 kDa or larger, having a main molecular weight peak at 70-80 kDa, were obtained through freeze-drying. A high-performance liquid chromatography (HPLC) result of the prepared *ginseng* berry polysaccharides is shown in FIG. 4.

[Preparation Example 2] Preparation of Red Ginseng Polysaccharides

Red *ginseng* polysaccharides were prepared in the same manner as in Preparation Example 1 except that red *ginseng* root was used instead of *ginseng* berry.

[Test Example 1] Detection of Arabinogalactan

For detection of the presence of arabino-β-3,6-galactan, the reactivity with a β-glucosyl Yariv reagent (Biosupplies, Parkville, Australia) was measured by single radical gel diffusion according to the method of Hoist and Clarke (Van Hoist G J, Clarke A E. Quantification of arabinogalactan-protein in plant extracts by single radial gel diffusion. *Anal. Chem.* 148: 446-450 (1985)).

Figure 5:
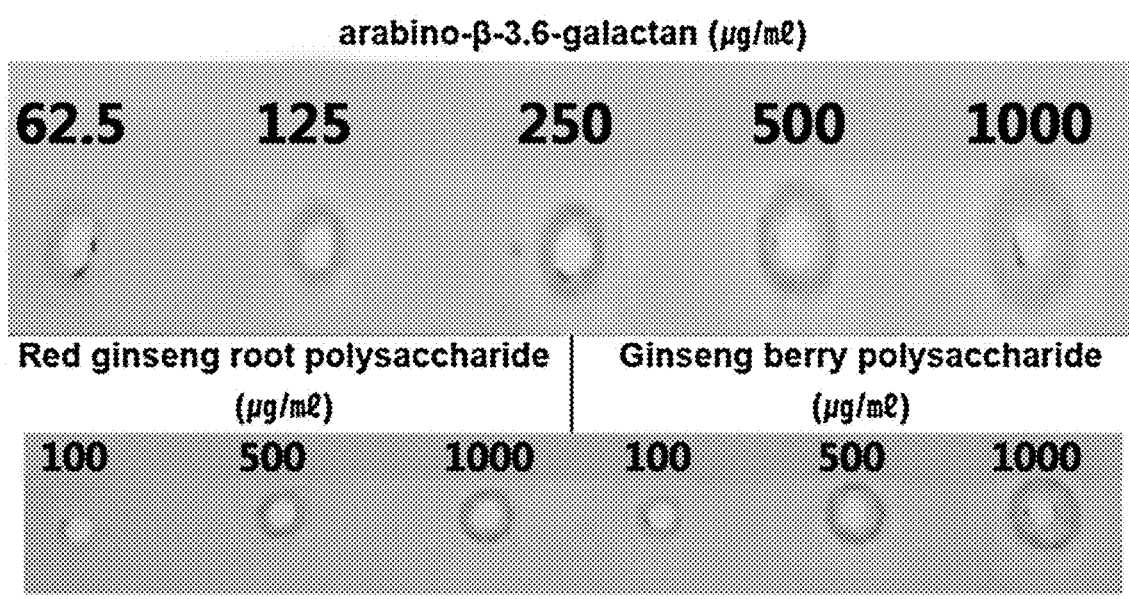
FIG. 5 shows the images of the precipitant rings of a reference material, *ginseng* berry polysaccharides and red *ginseng* root polysaccharides after treatment with a β-glucosyl Yariv reagent.

After preparing a 0.15 M NaCl agarose plate containing 10 μg/mL β-glucosyl Yariv reagent and preparing a well with a diameter of 2.5 mm, a solution containing gum arabic as a reference material and 5 μg of a sample, which were diluted to different concentrations, was injected into each well. After allowing the plate to stand in wet state for 15 hours and react, the presence of arabino-β-3,6-galactan was observed by observing the produced red precipitant ring. The reactivity between the sample and the β-glucosyl Yariv reagent was compared by calculating the area of the produced precipitant ring. As shown in FIG. 5, 62.5, 125, 250, 500 and 1000 μg/mL of the reference material and 100, 500 and 1000 μg/mL of the polysaccharides of Preparation Example 1 and Preparation Example 2 were used as samples.

Figure 6:
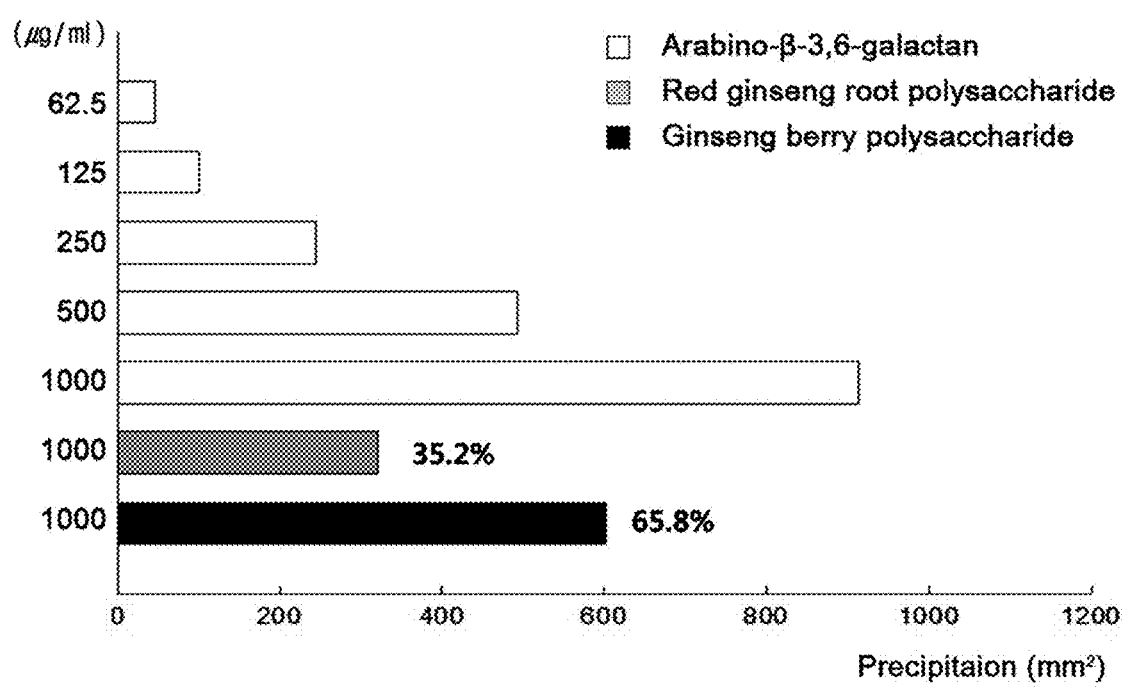
FIG. 6 compares the area of the precipitant rings of a reference material, *ginseng* berry polysaccharides and red *ginseng* root polysaccharides after treatment with a β-glucosyl Yariv reagent.
Figure 8:
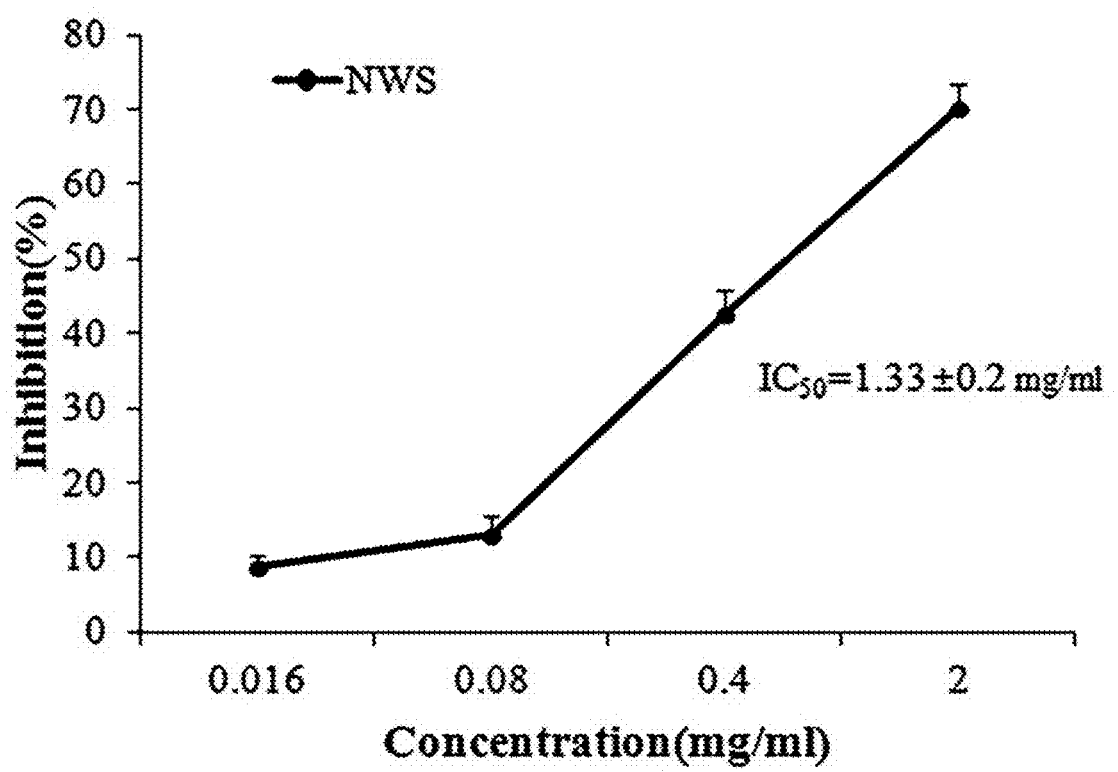
FIG. 8 shows a result of investigating inhibitory effect on neuraminidase activity upon inoculation of NWS virus to a *ginseng* berry polysaccharides-treated group.
Figure 9:
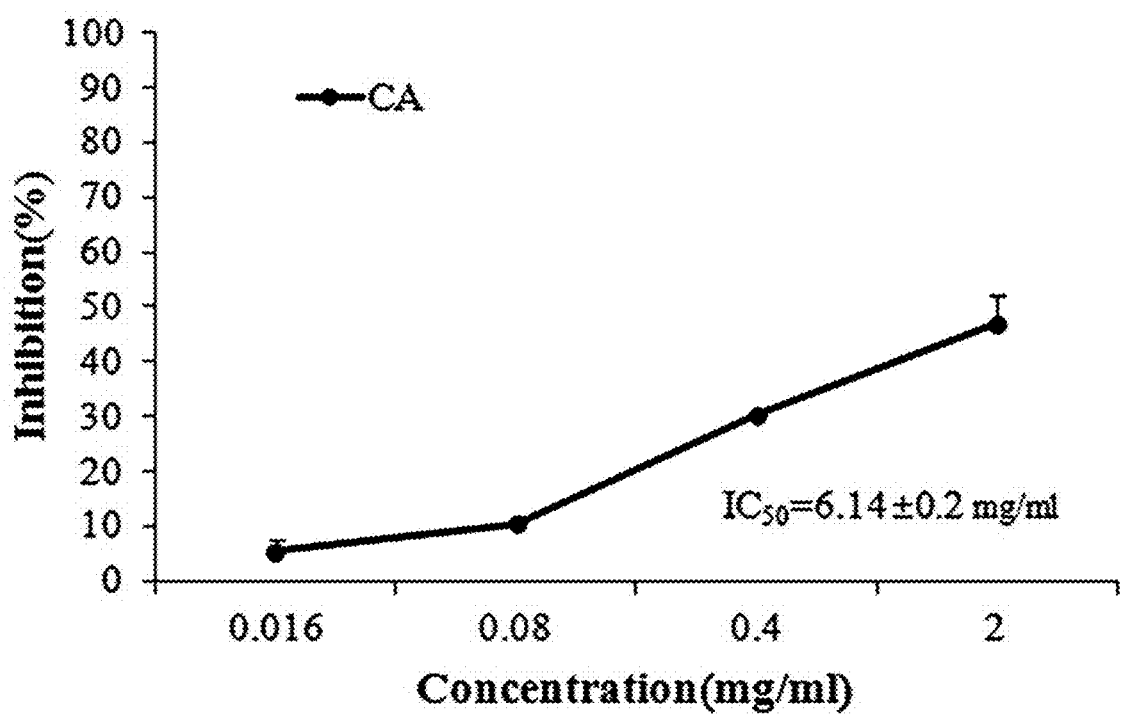
FIG. 9 shows a result of investigating inhibitory effect on neuraminidase activity upon inoculation of CA virus to a CVT-treated group.
Figure 10:
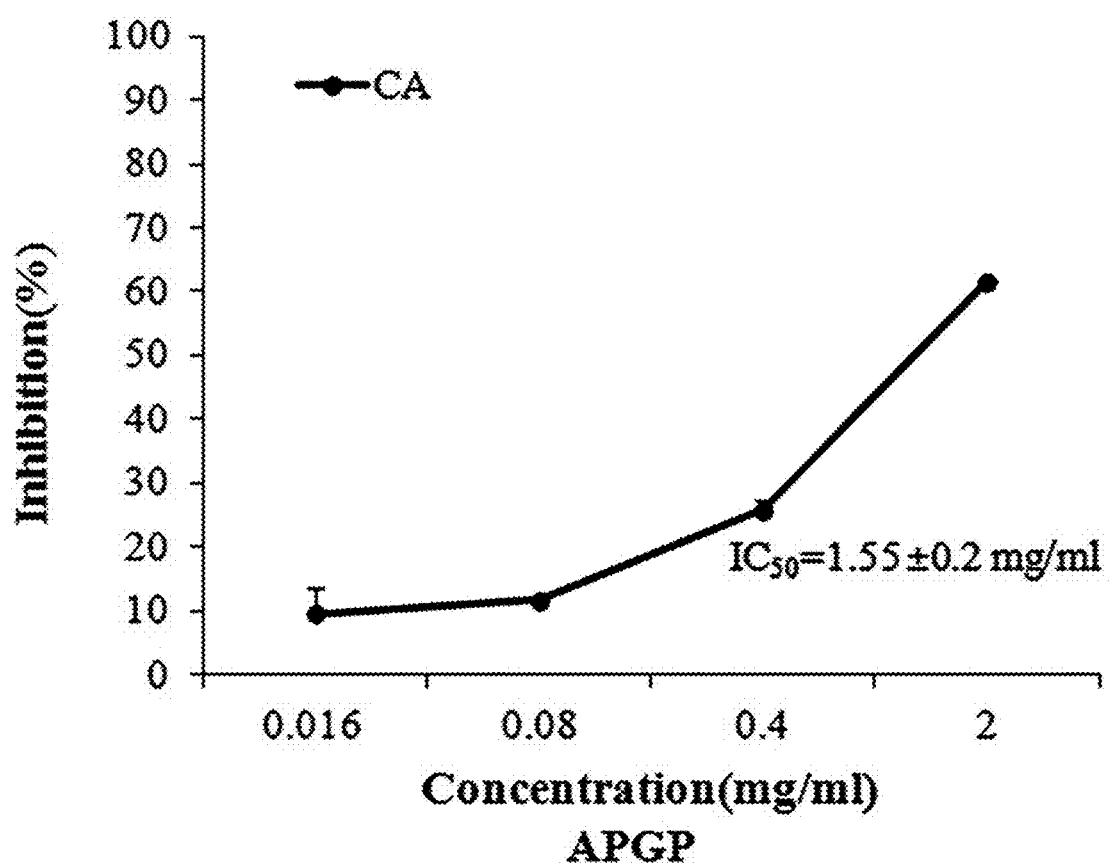
FIG. 10 shows a result of investigating inhibitory effect on neuraminidase activity upon inoculation of CA virus to a *ginseng* berry polysaccharides-treated group.

The relative content of arabino-β-3,6-galactan calculated from the measured area of the produced red precipitant ring is shown in FIG. 6. In FIG. 6, the area was compared for the groups treated with 1000 μg/mL of each sample with respect to the group treated with 1000 μg/mL of the reference material concentration.

From FIG. 6, it can be seen that the *ginseng* berry polysaccharides contain the arabinogalactan structure at a higher content of about 2 times as compared to the red *ginseng* polysaccharides.

[Test Example 2] Inhibition of Influenza Virus Proliferation by Ginseng Berry Polysaccharides The antiviral effect of the *ginseng* berry polysaccharides was investigated using canine kidney cell lines, MDCK (Madin-Darby canine kidney cells, ATCC: CCL-34).

After adding MDCK cells to a 96-well microplate, with $1 \times 10^5$ cells per well, the cells were cultured in an EMEM medium (penicillin 100 units, streptomycin 100 μg, 10% FBS). When the MDCK cells formed a monolayer, the cells were washed 2 times with an EMEM medium containing antibiotics only. H1N1 cells (influenza A virus subtype/H1N1/pdm) diluted to 100TCID50 were placed in an EP tube. After adding the *ginseng* berry polysaccharides of Preparation Example 1 (APGP) diluted to different concentrations as samples to each tube, reaction was conducted at 4° C. for 1 hour. As a positive control group sample, CVT-E002 (COLD-FX®, hereinafter "CVT"), which is an extract of American *ginseng* (*Panax quinquefolium*), was used. 1 hour later, the reaction solution was inoculated to pre-washed MDCK cells, at 3 wells per concentration, and incubated at 35° C. for 1 hour. 1 hour later, after removing all the medium from the plate and washing once with PBS, 100 mL of an EMEM medium supplemented with antibiotics and 10 μg/mL trypsin was aliquoted to each well and then incubation was conducted at 37° C. for 48-72 hours.

After culturing for 48-72 hours until cytopathic effect (CPE) occurred completely in a control group infected with the H1N1 strain and not treated with the sample, the state of the cells was observed every day with an inverted microscope. The cytopathic effect includes cell rounding due to infection and cell death after detachment. 48-72 hours after the culturing, in order to investigate cell viability, 10 mL of Cell Counting Kit-8 (Dojindo, Kumamoto, Japan, tetrazolium salt WST-8) was added to each well and absorbance was measured at 450 nm after incubation at 35° C. for 2 hours.

It was confirmed that the *ginseng* berry polysaccharides inhibited the cytopathic effect (CPE) of the MDCK cells treated with the influenza virus in the concentration ranges of 0.78125-3.125 mg/mL.

TABLE 1

| Sample | $CC_{50}$ (mg/mL) | $EC_{50}$ (mg/mL) | SI ($CC_{50}/EC_{50}$) |
|---|---|---|---|
| Cold-Fx (CVT) | 7.50 ± 1.91 | N/A | N/A |
| APGP | 4.69 ± 1.10 | 0.59 ± 0.36 | 7.95 |

Table 1 shows the selectivity indices (SI) of the samples. The $CC_{50}$ (50% cytotoxic concentration) value is the concentration of the sample which induces 50% of cell death, and a larger value means that the sample is safer. The $EC_{50}$ (50% inhibitory concentration) value is the concentration at which 50% of the virus is inhibited, and a smaller value means that the effect of inhibiting virus is superior.

A larger SI value means that the effect of inhibiting virus proliferation is superior. Whereas the control group CVT showed no antiviral effect at all, the *ginseng* berry polysaccharides showed a high value of 7.95. This value is remarkably higher than that of the biologically known single substances, EGCG (5.6) or resveratrol (2) (Kim, Y.; Narayanan, S.; Chang, K. O. Inhibition of influenza virus replication by plant-derived isoquercetin. *Antivir. Res.* 2010, 88, 227-235.), indicating the superior effect of inhibiting influenza virus.

[Test Example 3] Inhibition of Neuraminidase by Ginseng Berry Polysaccharides

The neuraminidase (NA) protein system on the virs surface of proliferating viruses such as influenza virus is used as an index for measuring antiviral activity against viruses. Neuraminidase activity inhibition test was conducted according to the method recommended by the WHO (standard operating procedure).

Neuraminidase inhibition activity was analyzed by the neuraminidase inhibitory IC50 using two mammalian-derived H1N1 virus strains NWS (A/NWS/33) and CA (A/California/07/2009). The virus strains was infected with MDCK cell line in an EMEM (Eagle's minimum essential medium) medium and a viral culture in which the virus was activated in the cell were used. The degree of neuraminidase activity inhibition depending on sample concentration was analyzed using the *ginseng* berry polysaccharides of Preparation Example 1 (APGP) as a sample and CVT-E002 (COLD-FX®, hereinafter "CVT"), which is an extract of American *ginseng* (*Panax quinquefolium*), as a positive control group.

After reacting 10 µL of the sample solution (APGP, CVT) at different concentrations with 50 µL of the viral culture at room temperature for 45 minutes, 50 µL of 200 µM MUNANA substrate (2'-(4-methylumbelliferyl)-α-D-N-acetylneuraminic acid) was added. After conducting reaction for 1 hour, 100 µL of a stop solution wherein 0.14 M NaOH was dissolved in 83% ethanol was added to terminate the reaction. Then, the inhibition of enzyme activity was calculated by measuring fluorescence at Ex. 360 nm/Em. 440 nm using a spectrofluorophotometer (ABI/Perkin Elmer Biosystems). The inhibition ratio (%) was calculated with respect to the fluorescence value of the control group not treated with the sample as 100%. The result is shown in FIGS. 7-10.

From FIGS. 7-10, it can be seen that the *ginseng* berry polysaccharides inhibit the neuraminidase activity in a concentration-dependent manner, and the *ginseng* berry polysaccharides exhibit remarkably superior effect of inhibiting neuraminidase activity with the $IC_{50}$ value of about ¼-⅕ as compared to the positive control group CVT.

Figure 11:
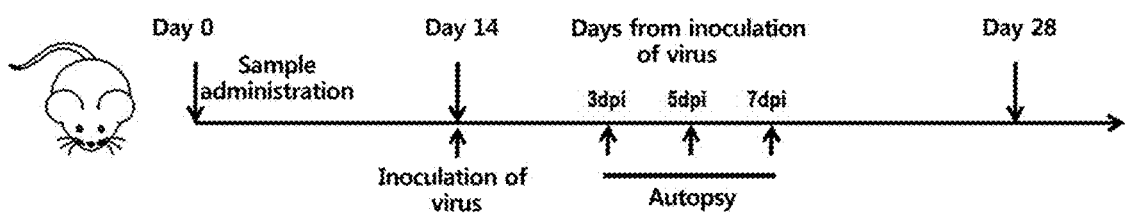
FIG. 11 schematically shows an influenza infection experiment schedule for an animal model in Test Example 4.

[Test Example 4] Influenza Virus Infection in Animal Model 0.5 mg/kg, 5 mg/kg or 50 mg/kg of a *ginseng* berry extract (APGP), as a sample, or 200 mg/kg of CVT-E002 (COLD-FX®, hereinafter "CVT"), which is an extract of American *ginseng* (*Panax* quinquefolium), as a positive control group, was orally administered to 7-week-old mouse (SPF BALB/c mouse) using a zoned for mouse. The sample was administered from 14 days before inoculation of virus, once a day. Influenza virus (influenza A virus subtype/H1N1/NWS strain) was inoculated intranasally at a dose of LD0 or LD70 after anesthetizing the mouse with ether. FIG. 11 schematically shows the influenza virus infection experiment schedule. The untreated control group (negative control) was administered with PBS instead of the sample without inoculation of virus, and the virus control group (virus control) was administered with PBS instead of the sample with inoculation of virus.

The infected mouse was subjected to tissue lesion and viral re-isolation experiments on days 3 (3 dpi), 5 (5 dpi) and 7 (7 dpi) after the inoculation of the virus.

[Test Example 5] Analysis of Histopathological Lesion in Animal Model

After sacrificing the mouse inoculated with influenza virus in Test Example 4 on days 3 (3 dpi), 5 (5 dpi) and 7 (7 dpi) after the inoculation of the virus, lung tissue was isolated and used for histopathological lesion analysis through H&E staining. FIGS. 15-18 show the images of the images of the lung lesion tissues. The number of the lesions was counted and quantified, and the lung index was calculated therefrom with respect to that of the untreated control group (negative control) as 100%. The result is shown in FIGS. 12-14.

Figure 12:
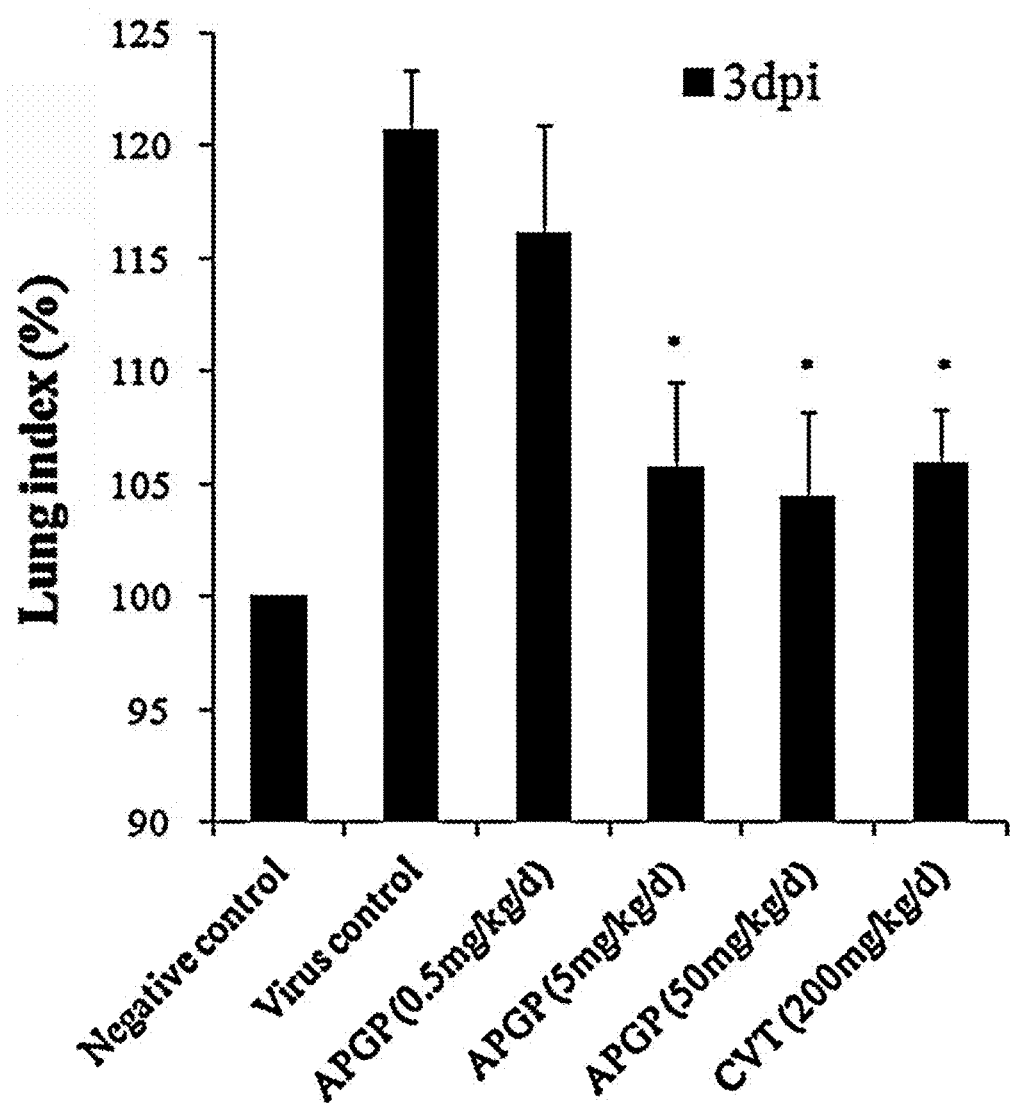
FIG. 12 shows lung lesion indices 3 days after inoculation of virus.
Figure 13:
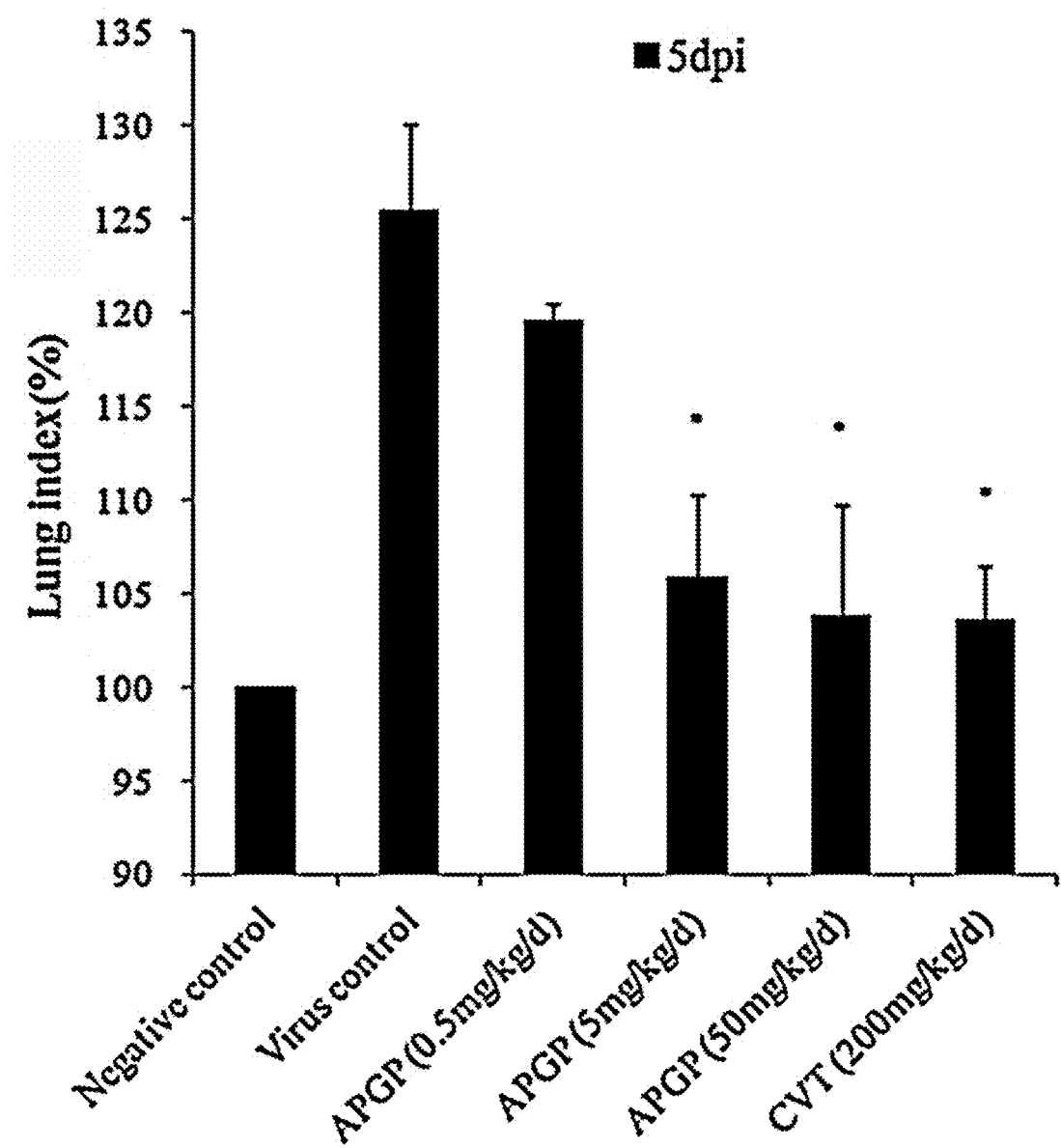
FIG. 13 shows lung lesion indices 5 days after inoculation of virus.
Figure 14:
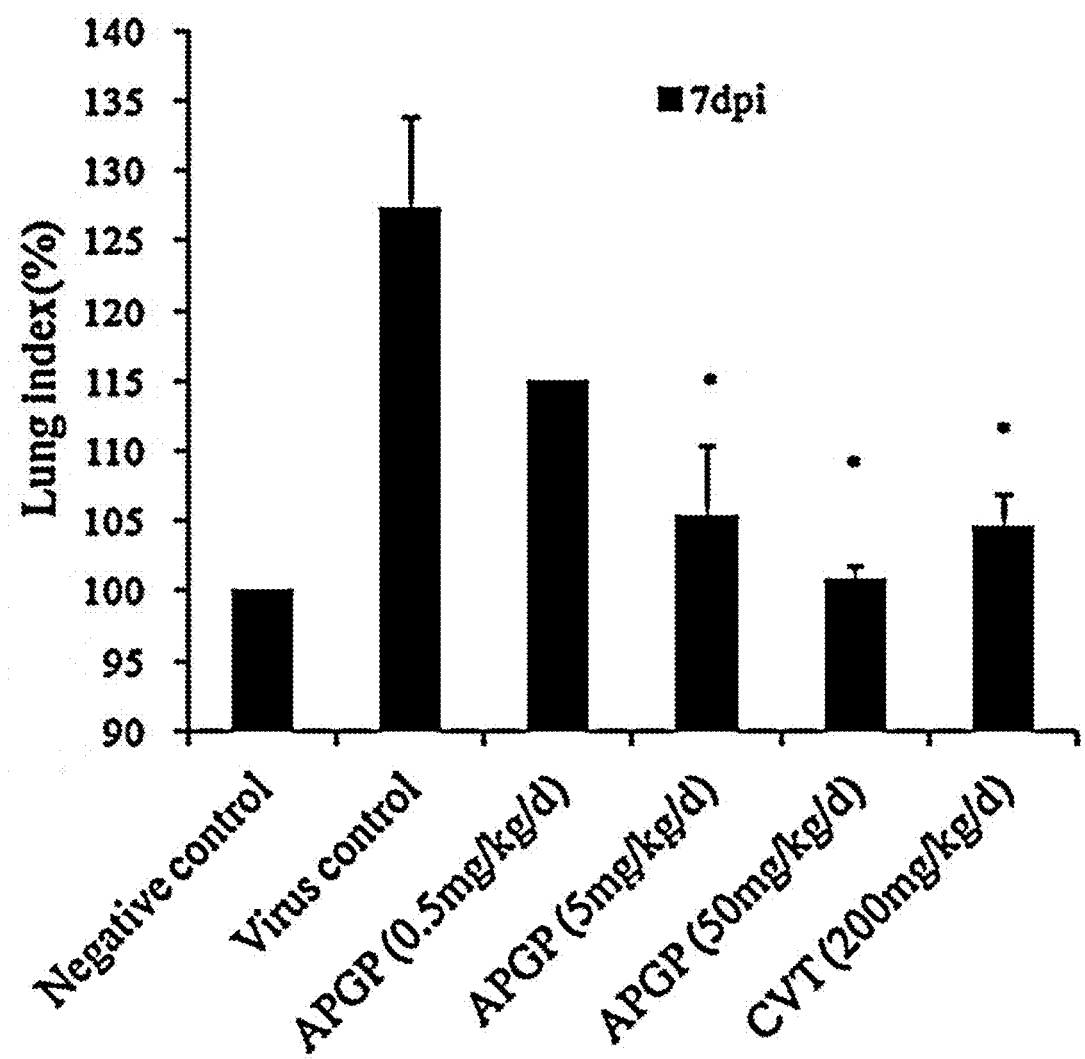
FIG. 14 shows lung lesion indices 7 days after inoculation of virus.
Figure 15:
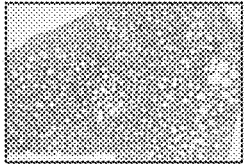
FIG. 15 shows the images of lung lesion tissue 3 days after inoculation of virus when *ginseng* berry polysaccharides were administered.
Figure 16:
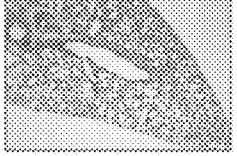
FIG. 16 shows the images of lung lesion tissue 7 days after inoculation of virus for a CVT-administered group, a positive control group and a negative control group.
Figure 17:
FIG. 17 shows the images of lung lesion tissue 3 days after inoculation of virus when *ginseng* berry polysaccharides were administered.

From FIGS. 12-14, it can be seen that the oral administration of the *ginseng* berry polysaccharides alleviates the lung index. In particular, it can be seen that, for the positive control group CVT, an amount corresponding to 40 times the administration dose of the *ginseng* berry polysaccharides is necessary to achieve an effect comparable to that of the *ginseng* berry polysaccharides.

[Test Example 6] Analysis of Viral Re-Isolation

After sacrificing the mouse inoculated with influenza virus in Test Example 4 on days 3 (3 dpi), 5 (5 dpi) and 7 (7 dpi) after the inoculation of the virus, lung tissue was isolated and RNA was extracted therefrom. After establishing a cDNA library with the extracted RNA using a cDNA synthesis kit and conducting quantitative RT-PCR, the number of re-isolated virus copies was counted and the degree of viral infection was determined. The result is shown in FIGS. 19-21.

Figure 19:
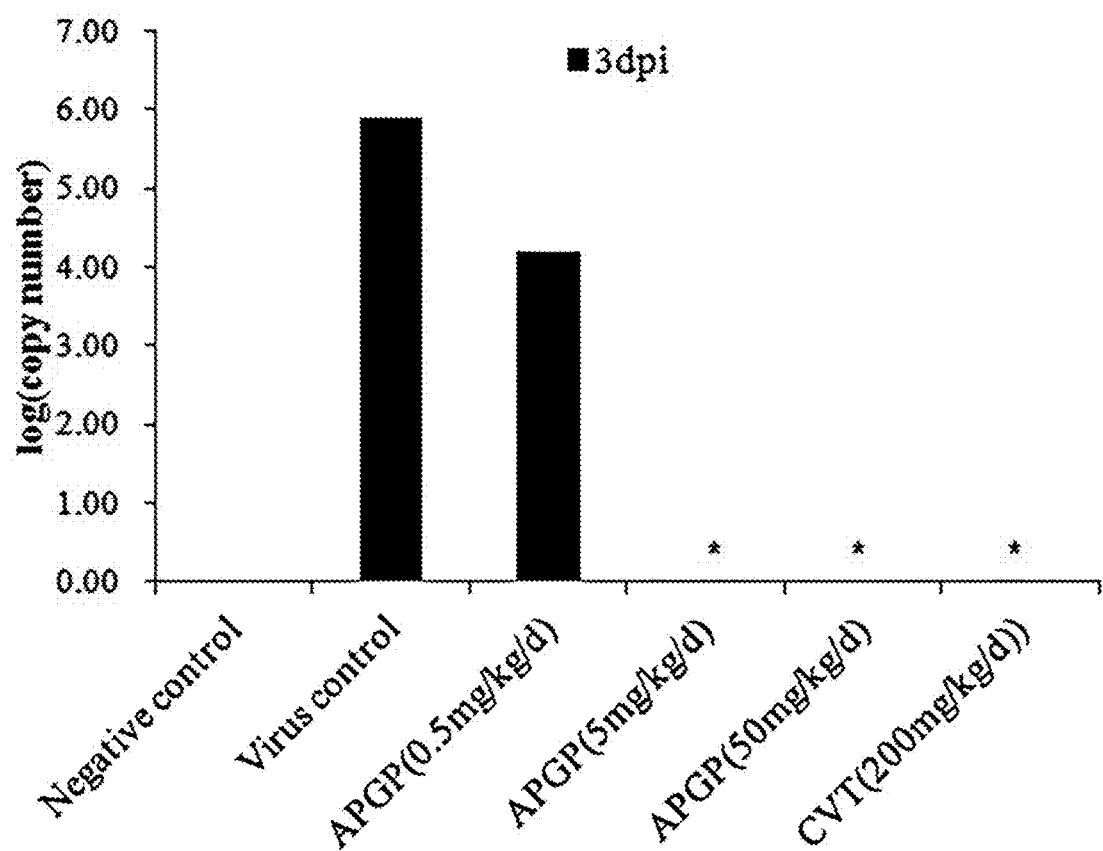
FIG. 19 shows a RT-PCR result of investigating the level of viral infection 3 days after inoculation of virus.
Figure 20:
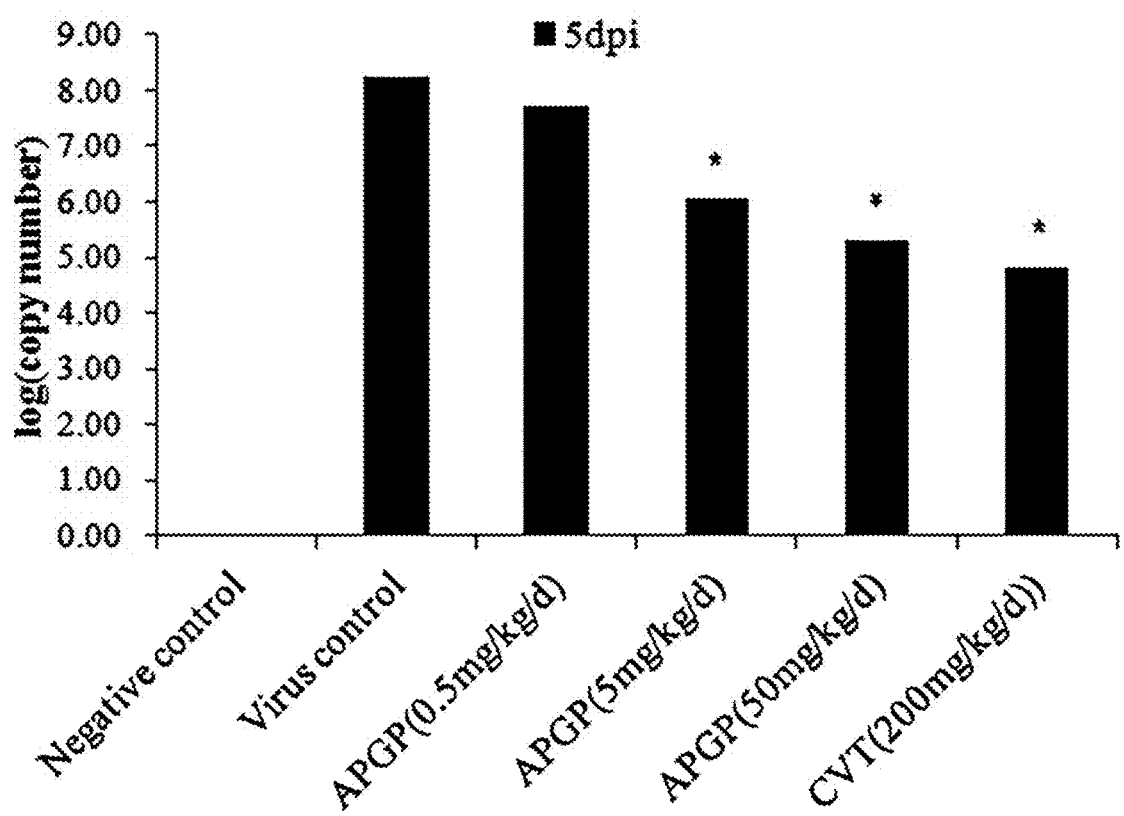
FIG. 20 shows a RT-PCR result of investigating the level of viral infection 5 days after inoculation of virus.
Figure 21:
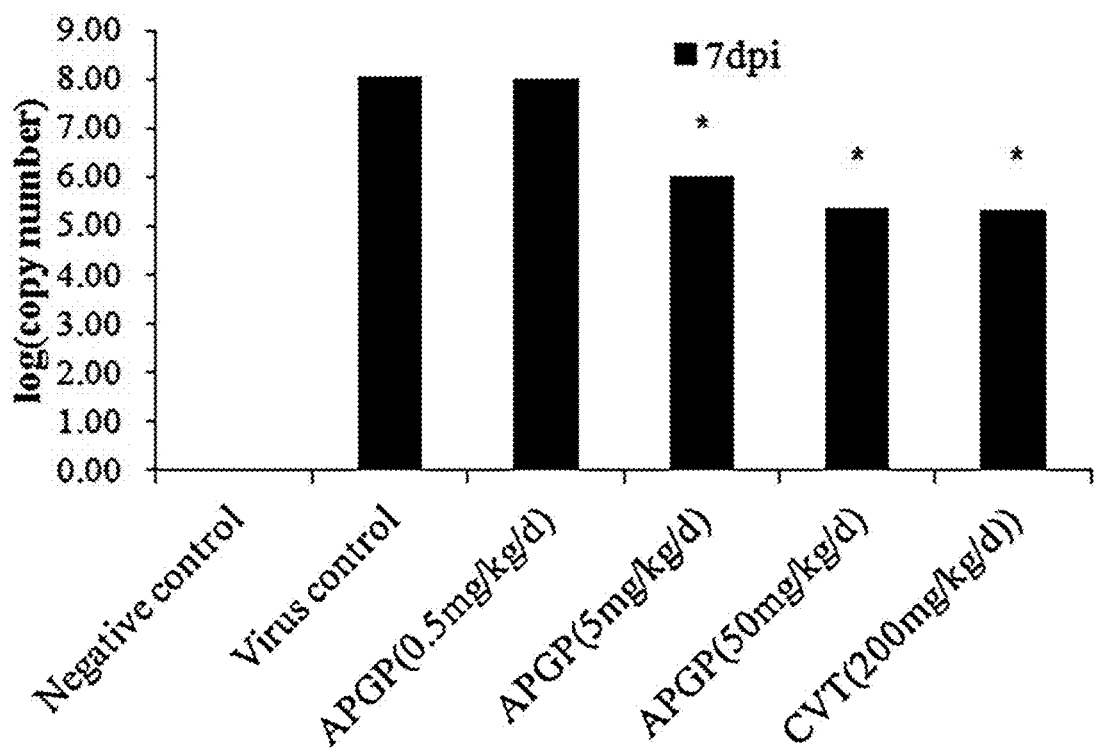
FIG. 21 shows a RT-PCR result of investigating the level of viral infection 7 days after inoculation of virus.

From FIGS. 19-21, it can be seen that the degree of viral infection is decreased remarkably by the administration of the *ginseng* berry polysaccharides. In particular, FIG. 19 shows that the groups administered with the *ginseng* berry polysaccharides at 5 or 50 mg/kg/day show no viral infection until day 3 after the inoculation of the virus. Thorough this, it can be seen that the *ginseng* berry polysaccharides can exhibit a superior effect of preventing influenza virus infection. In addition, it can be seen that, for the positive control group CVT, an amount corresponding to 40 times the administration dose of the *ginseng* berry polysaccharides is necessary to achieve an effect comparable to that of the *ginseng* berry polysaccharides.

The invention claimed is:

1. A method for inhibiting influenza virus infection which comprises administering an effective amount of a composition comprising *ginseng* (*Panax ginseng* C. A. Meyer) berry polysaccharides to a subject in need of inhibition of influenza virus,
   wherein the *ginseng* berry polysaccharides comprise galacturonic acid and glucuronic acid, and wherein the *ginseng* berry polysaccharides exhibit reactivity of 40% or higher when treated with a β-glycosyl Yariv reagent with respect to a reference arabino-β-3,6-galactan as 100%.

2. The method according to claim 1, wherein the *ginseng* berry polysaccharides further comprise arabinose and galactose.

3. The method according to claim 1, wherein the galacturonic acid and the glucuronic acid are comprised in an amount of 0.1-25 wt % based on the total weight of the *ginseng* berry polysaccharides.

4. The method according to claim 1, wherein the *ginseng* berry polysaccharides are derived from water soluble ingredients in an ethanol-insoluble fraction of *ginseng* berry.

5. The method according to claim 1, wherein the *ginseng* berry polysaccharides inhibit the neuraminidase activity of influenza.

6. The method according to claim 1, wherein the influenza comprises one or more of H1N1, H1N2, H2N2, H3N2, H5N1, H6N1, H7N2, H7N3, H7N7, H7N9, H9N2, and H10N7.

7. The method according to claim 1, wherein the composition is for functional health food.

8. The method according to claim 1, wherein the composition is a pharmaceutical composition.

* * * * *